US006680376B2

(12) United States Patent
Chiou

(10) Patent No.: US 6,680,376 B2
(45) Date of Patent: Jan. 20, 2004

(54) PROCESS FOR SELECTIVELY ISOLATING AVIAN IMMUNOGLOBULINS

(75) Inventor: Victor Chiou, Taichung (TW)

(73) Assignee: Good Biotech Corporation, Taichung (TW)

( * ) Notice: Subject to any disclaimer, the term of this patent is extended or adjusted under 35 U.S.C. 154(b) by 33 days.

(21) Appl. No.: 09/733,210

(22) Filed: Dec. 8, 2000

(65) Prior Publication Data

US 2002/0107367 A1 Aug. 8, 2002

(51) Int. Cl.$^7$ .................. G01N 33/08; C07K 16/02; C07K 17/02; C07K 1/14
(52) U.S. Cl. .................. 530/413; 530/389.1; 530/861
(58) Field of Search .................. 530/389.1, 415, 530/416, 412, 413, 417, 418, 853; 424/85.1, 85.5, 581

(56) References Cited

U.S. PATENT DOCUMENTS

| | | | |
|---|---|---|---|
| 4,511,473 A | * | 4/1985 | Hou et al. |
| 4,550,019 A | | 10/1985 | Polson |
| 5,340,923 A | * | 8/1994 | Carroll et al. |
| 5,367,054 A | | 11/1994 | Lee |
| 5,585,098 A | | 12/1996 | Coleman |
| 5,601,823 A | | 2/1997 | Williams et al. |
| 5,728,813 A | | 3/1998 | Lyman et al. |
| 5,922,359 A | * | 7/1999 | Youssefyeh et al. |
| 5,976,519 A | | 11/1999 | Nojiri et al. |

FOREIGN PATENT DOCUMENTS

| | | |
|---|---|---|
| DE | 100 29 705 A1 | 1/2002 |
| DE | 100 65 227 A1 | 7/2002 |
| EP | 0 503 293 A1 | 9/1992 |
| JP | 64-38098 | 2/1989 |

OTHER PUBLICATIONS

Higgins et al., Vet Immunol. Immunopathol 44(2): 169–80, 1995.*
Narhi et al Analytical Biochemistry 253: 236–245, 1997.*
Harlow et al in Antibodies a Laboratory Manual, 1998, Cold Spring harbor laboratory publication, Cold Spring Harobr, NY, pp. 298–299, 292–293, and 658.*
Hansen et al., "Isolation and purification of immunoglobulins from chicken eggs using thiophilic interaction chromatography", *J. Immunol. Methods* 215:1–7 (1998).
Behn et al., "Use of Polyclonal Avian Antibodies", *Springer Lab Manuals. Chicken Egg Yolk Antibodies, Production and,* 108–210 (2001).
Staak et al., "Isolation of IgY from Yolk", *Springer Lab Manuals. Chicken Egg Yolk Antibodies, Production and,* 65–107 (2001).
Warr et al., "IgY: clues to the origins of modern antibodies", *Immunology Today* 16(8):392–398 (1995).

Akita et al., "Comparison of Four Purification Methods for the Production of Immunoglobulins from Eggs Laid by hens immunized with an Enterotoxigenic *E. coli* Strain", Journal of Immunological Methods 160:207–214, 1993.
Akita et al., "Immunoglobulins from Egg Yolk: Isolation and Purification", Journal of Food Science 57:629–634, 1992.
Akita et al., "Production and Purification of Fab Fragments from Chicken Egg Yolk Immunoglobulin Y(IgY)", Journal of Immunological Methods 162:155–164, 1993.
Brussow et al., "Bovine Milk Immunoglobulins for Passive Immunity to Infantile Rotavirus Gastroenteritis", Journal of Clinical Microbiology 25:982–986, 1987.
Jens Chr Jensenius et al., "Eggs: Conveniently Packaged Antibodies, Methods for Purification of Yolk IgG", Journal of Immunological Methods 46:63–68, 1981.
Gottstein et al., "Egg Yolk Immunoglobulin Y as an Alternative Antibody in the Serology of Echinococcosis", Z. Parasitenkd 71:273–276, 1985.
Grey, "Duck Immunoglobulins I. Structural Studies on a 5.7S and 7.8S γ–Globulin", Journal of Immunology 98:811–819, 1967.
Hassl et al., "Purification of Egg Yolk Immunoglobulins A Two–step Procedure Using Hydrophobic Interaction Chromatography and Gel Filtration", Journal of Immunolgical Methods 110:225–228, 1988.
Hatta et al., "Separation of Phospholipids from Egg Yolk and Recovery of Water–Soluble Proteins", Journal of Food Science 53:425–431, 1988.
Litman et al., "Active Sites of Turtle and Duck Low Molecular Weight Antibody to 2'4'Dinitrophenol", Immunochemistry 10:323–329, 1973.
Magor et al., "Structural Relationship Between the Two IgY of the Duck, Anas Platyrhynchos: Molecular Genetic Evidence", The Journal of Immunology 149:2627–2633, 1992.
Muratsugu et al., "Adsorption and Desorption of F(ab')$_2$ Anti–hIgG on Plasma–Polymerized Allylamine Thin Film: The Application of the Film to Immunoassay", Journal of Colloid and Interface Science 147:378–386, 1991.
Ortega–Vinuesa et al., "Particle Enhanced Immunoaggregation of F(ab')$_2$ Molecules", Journal of Immunological Methods 190:29–38, 1996.
Polson et al., "Isolation of Viral IgY Antibodies from Yolks of Immunized Hens", Immunological communications 9:475–493, 1980.

(List continued on next page.)

*Primary Examiner*—Christina Chan
*Assistant Examiner*—Phuong N. Huynh
(74) *Attorney, Agent, or Firm*—Fish & Richardson P.C.

(57) ABSTRACT

This invention relates to a method for selectively isolating IgY(ΔFc) avian antibodies from IgY avian antibodies. For example, the method includes: (a) providing an aqueous fraction from yolk of an egg of an anseriform bird; (b) precipitation IgY antibodies using a first precipitant salt; and (c) precipitating the IgY(ΔFc) antibodies from a supernatant using a second precipitant salt to provide an isolated preparation enriched for IgY(ΔFc) antibodies.

36 Claims, 4 Drawing Sheets

OTHER PUBLICATIONS

Tacket et al., "Protection by Milk Immunoglobulin Concentrate Against Oral Challenge with Enterotoxigenic *Escherichia coli*", The New England Journal of Medicine 318:1240–1243, 1988.

Toth et al., "Humoral Immune Response of the Duck to Duck Hepatitis Virus: Virus–Neutralizing vs. Virus–Precipitating Antibodies", Avian Diseases 25:17–28, 1980.

Unanue et al., "V. Studies on the Interaction of Nephrotoxic Antibodies with Tissues of the Rat", Experimental Glomerulonephritis 697–714, 1965.

Zimmerman et al., "Structural Studies on the Duck 5.7S and 7.8S Immunoglobulins", Biochemistry 10:482–488, 1971.

Losonczy et al., "ELISA for the measurement of IgY concentrations of hen's and quail's serum and yolk", INABIS 2000, $6^{th}$ Internet World Congress for Biomedical Sciences, Poster#47.

Otani et al., Lebsensm.–Wiss. U.–Technol., vol. 24:152–158 (1991).

Lamoyi, "Preparation of F(ab')$_2$ Fragments from Mouse IgG of Various Subclasses", Methods In Enzymology 62:652–663 (1986).

U.S. patent application Ser. No. 09/591,665, Chiou, filed Jun. 9, 2000.

* cited by examiner

PROCESS FOR SELECTIVELY ISOLATING AVIAN IMMUNOGLOBULINS

BACKGROUND OF THE INVENTION

1) Field of the Invention

The present invention relates to a method for rapid isolation and purification of yolk antibodies, in particular IgY(ΔFc) antibody, from avian yolk, and the yolk antibodies produced thereby. More particularly, the present invention relates to a method for isolation and purification of yolk antibodies from avian yolk by an adsorption chromatographic procedure using a water insoluble non-charged absorbent to accomplish a desired separation of the aqueous and lipidic phases, and by a salting-out procedure that differentially precipitates the yolk antibodies. The present invention also relates to uses of the yolk antibodies in quantitative or qualitative immunoassay or in the preparation of pharmaceutical compositions directing to an etiological agent of interest.

2) Description of the Related Art

Antibodies are used widely in many biological investigations and clinical applications. Sera obtained from hyperimmunized mammalians are the most common source of polyclonal antibodies. Antibodies derived from such immune sera belong to a group of proteins called "immunoglobulins," among which the immunoglobulin G (IgG) is the most abundant. The IgG molecule consists of three domains, namely two Fab regions and one Fc region. The Fab portion involves mainly in antigen binding. The Fc portion, though having no ability to bind with an antigen, directs several biological activity of an antibody, such as complement fixing and Fc receptor binding.

In the art of immunodiagnostics, an intact IgG molecule is not suitable for use in detection systems and immunological assays involving mammalian sera since the Fc region on an IgG molecule is capable of binding to Fc receptors, activating the complement system, and reacting with rheumatoid factor in mammalian sera. Removal of the Fc portion of an IgG molecule frequently lead to a reduction in the interference (E. Lamoyi, *Methods in Enzymology* 121:652–663. (1986)).

Some of the suggested uses of antibody in immunotherapy include treating patients with intoxicated bacterial toxins or snake venoms (see, for example, U.S. Pat. Nos. 5,340,923 and 5,601,823), and protection of neonatal piglets against fatal enteric colibacillosis (see, for example, H. Brussow et al., *J. Clin. Microbiol.* 25:982 (1987); and C. O. Tacket et al., *New Eng. J. Med.* 318:1240 (1988)). Since the Fc fragment of an antibody molecule is known to be the most antigenic portion of the immunoglobulin (E. M. Akita et al., *J. Immunol. Methods.* 162:155–164 (1993)), cleavage of the same which results in the formation of an F(ab')$_2$ fragment will reduce significantly a number of potential allergenic sites on the immunoglobulin molecule and is thus beneficial to human or an animal administered with the immunoglobulin.

Recently, the divalent F(ab')$_2$ antibody fragment has been shown to be more useful in the immunodiagnostic tests (M. Muratsugu et al., *J. Colloid Interface Sci* 147:378 (1991); and J. L. Ortega-Vinuesa et al., *J. Immunol Methods* 90:29 (1996)) and more suitable for development of the immunoassays involving mammalian sera than the parent IgG.

The F(ab')$_2$ antibody fragment, however, has not found widespread use in clinical immunodiagnostic kits as one might expect. This may be attributed to the difficulties and cost-ineffectiveness of large scale production of the F(ab')$_2$ fragments, which is conventionally made by pepsin digestion of IgG and subsequent purification via chromatography.

Ducks and their phylogenetically close relatives and some reptiles, such as turtles, have three kinds of serum immunoglobulins: a macromolecular immunoglobulin IgM (800 kDa in duck), and two isoforms of low molecular weight IgG with sedimentation coefficients of 7.8S (in duck, 180 kDa) and 5.7S (in duck, 130 kDa), respectively. (E. R. Unanue et al., *J. Exp. Med.* 121:697–714 (1965); H. M. Grey, *J. Immunol* 98:811–819 (1967); and B. Zimmerman et al., *Biochemistry* 10:482–448 (1971)). Avian IgG is oftentimes called IgY due to their existence in egg yolk. The 5.7S IgY, constituted with shorter heavy chains, is structurally and antigenically similar to the F(ab')$_2$ fragment of the 7.8S IgY (FIG. 1), and this fact leads to the nomenclature of IgY (equivalent to 7.8S IgY) and IgY(ΔFc) (equivalent to 5.7S IgY) to represent both isoforms of IgY (K. E. Magor et al., *J. Immunol.* 149:2627–2633 (1992)).

Studies conducted in the infected or experimentally immunized birds showed that duck antibodies are deficient in a number of biological effector functions, including complement fixation and Fc receptors binding, without sacrificing their binding activity to corresponding antigens (G. W. Litman et al., *Immunochemistry* 10:323 (1973); and T. E. Toth et al., *Avian Dis.* 25:17–28 (1981)). This may reasonably result from the apparent lack of Fc-equivalent region of the IgY(ΔFc) antibody that constitutes the quantitatively major component of duck antibody response. It is thus believed that the IgY(ΔFc) antibody, which appears to be a structural and functional analog of the F(ab')$_2$ fragment, would provide magnificent advantages in immunological uses, if a promising process for manufacturing the antibody could be found, and the appropriate physical requirements for its activity could be identified.

Avian yolk antibodies have been reported to exhibit useful properties for both research and clinical applications as mammalian antibodies do (see, for example, U.S. Pat. Nos. 5,340,923; 5,585,098; 5,601,823; and 5,976,519). Egg yolks derived from a laying hen is inexpensive and more convenient and safer to handle as compared to the hyperimmunized mammalian sera. More importantly, yolk antibodies are able to stand up to the scrutiny under modern animal protection regulations (A. Poison et al., *Immunol. Commun.* 9:475 (1980); and B. Gottstein et al.). These facts suggest a potential use of egg yolk as a commercial source of antibodies.

However, high contents of lipidic substances, such as fatty acids, cholesterol and lecithin, in egg yolk make the isolation of yolk antibodies a cumbersome and laborious task. Many efforts have been made in this regard. For instance, water soluble precipitants, including agar, pectin (Japanese Kokai No. 64-38098 published in Feb. 8, 1989), dextran sulfate (J. C. Jensenius et al., *J. Immunol. Methods* 46:63 (1981)), natural gums (H. Hatta et al., *J. Food Science* 53:425(1988)) and polyethylene glycol (PEG) (A. Poison et al., *Immunol. Invest.* 14:323 (1985); see also U.S. Pat. No. 4,550,019 issued to A. Poison) were used to precipitate non-aqueous bio-molecules, mainly lipids and yolk granules, to thereby harvest a water soluble phase containing abundant yolk antibodies. A. Hassl et al. developed a two-step chromatographic process, comprised of hydrophobic interaction chromatography and size exclusive chromatography, for further isolation of yolk antibodies from a PEG-purified fraction (A. Hassl and H. Aspock, *J. Immunol. Methods* 110:225 (1988)). Akita et al. described an improved method for isolating IgY, in which yolk antibodies were extracted from chick eggs by diluting the egg yolks with a large volume of water and subjecting the resultant supernatant to size exclusive chromatography and/or ion exchange chromatography (E. M. Akita et al., *J. Immunol. Methods.* 160:207 (1993); and E. M. Akita and S. Nakai, *J. Food Sci.* 57:629 (1993)).

However, all these studies and patents focus on the isolation of the entire population of yolk antibodies (which includes at least IgY and IgY(ΔFc)) from avian eggs, rather than on the purification of IgY(ΔFc) antibody alone. Moreover, since IgY(ΔFc) antibodies are present only in birds belonging to the Order Anseriformes, including duck and goose, and since the lipid content in the egg yolk of the aniserform birds is reported higher than that in the galliform birds, such as chicken and turkey, the conventional methods described above provide no suggestion of a successful purification of IgY(ΔFc) antibody.

Therefore, there exists a need for a rapid, cost-effective and high-throughput process that provides easy isolation of the desired IgY(ΔFc) antibody from the antibody pool of avian egg while maintaining the activity of the IgY(ΔFc) antibody. The substantially purified IgY(ΔFc) antibody may acts as a new type of F(ab')$_2$ antibody for various immuno-diagnostic and immunotherapeutic uses.

SUMMARY OF THE INVENTION

An extensive research has been conducted to fulfill the industrial requirements for yolk antibodies as indicated above. It has now been unexpectedly found that a successful isolation of yolk antibodies from avian yolks can be readily accomplished through an adsorption chromatographic procedure using a water insoluble non-charged absorbent, and/or through a simple salting-out procedure that differentiates different isoforms of the yolk antibodies. According to the process of the present invention, the highly purified yolk antibodies, in particular the highly purified IgY(ΔFc), can be easily obtained with high yield in an economic manner, and are ready for a wide variety of immunological uses.

Accordingly, an object of the present invention is to provide a process for selectively isolating antibody isoforms from egg yolk, comprising the steps of:

(i) obtaining an aqueous fraction of egg yolk from a fowl hen egg;

(ii) a major portion of a first isoform of antibodies from the aqueous fraction of step (i) by salting out the aqueous fraction with a first non-denaturing salt of a first concentration; and (iii) salting out a major portion of a second isoform of antibodies from the resultant aqueous fraction of step (ii) by adjusting the resultant aqueous fraction from step (ii) with a second non-denaturing salt of a second concentration;

with a proviso that when the first non-denaturing salt and the second non-denaturing salt are the same, the first and second concentrations are different.

Another object of this invention is to provide a process for isolating antibody from egg yolk, in which an absorbent is used to remove the majority of lipidic and caseinaceous matter normally present in egg yolk.

The present invention thus provides a process for isolating antibody from egg yolk, comprising the steps of:

(a) removing non-aqueous bio-molecules and granules from the egg yolk of a fowl hen egg to thereby obtain a water-miscible fraction containing yolk antibodies;

(b) passing the water-miscible fraction through a stationary phase containing an effective amount of a water insoluble non-charged absorbent capable of adsorbing water-miscible lipidic substances normally present in egg yolk;

(c) collecting the solution which has flowed through the stationary phase; and (d) recovering the yolk antibodies from the flow-through solution of step (c).

The present invention also provides an alternative process for isolating antibody from egg yolk, comprising the steps of:

(a) removing non-aqueous bio-molecules and granules from the egg yolk of a fowl hen egg to thereby obtain a water-miscible fraction containing yolk antibodies;

(b) passing the water-miscible fraction through a stationary phase containing an effective amount of a water insoluble non-charged absorbent capable of adsorbing water-miscible lipidic substances normally present in egg yolk;

(c) eluting the stationary phase to obtain an eluate; and (d) recovering the yolk antibodies from the eluate of step (c).

According to the process of this invention, an abundant amount of a selected isoform of yolk antibodies, in particular IgY(ΔFc) antibody, available for various industrial applications can be obtained in an economic, efficient and time-saving manner.

It is still another object of the invention to provide the clinical and research uses of the IgY(ΔFc) antibody so produced. In addition to the cost-effectiveness and ease of preparation, the IgY(ΔFc) antibody according to the present invention has advantages of being inactive to the complement system and rheumatoid factors in mammalian sera, and having poor cross-reactivity to mammalian IgG, and is thus particularly suitable for use in immunological assays involving mammalian sera with minimal interference. It would be appreciated by those skilled in the art that the IgY(ΔFc) antibody can be present in the form of a single reagent for clinical, research and other applications, or included in a commercial kit as an active component.

It is another specific object of the invention to provide a reagent for immunoassay of an etiological agent of interest, comprising an IgY(ΔFc) antibody obtained by the process according to this invention.

BRIEF DESCRIPTION OF THE DRAWINGS

The above and other objects and features of the present invention will become apparent with reference to the following description of the preferred embodiments taken in conjunction with the accompanying drawings, in which.

DETAILED DESCRIPTION OF THE INVENTION

Figure 1:
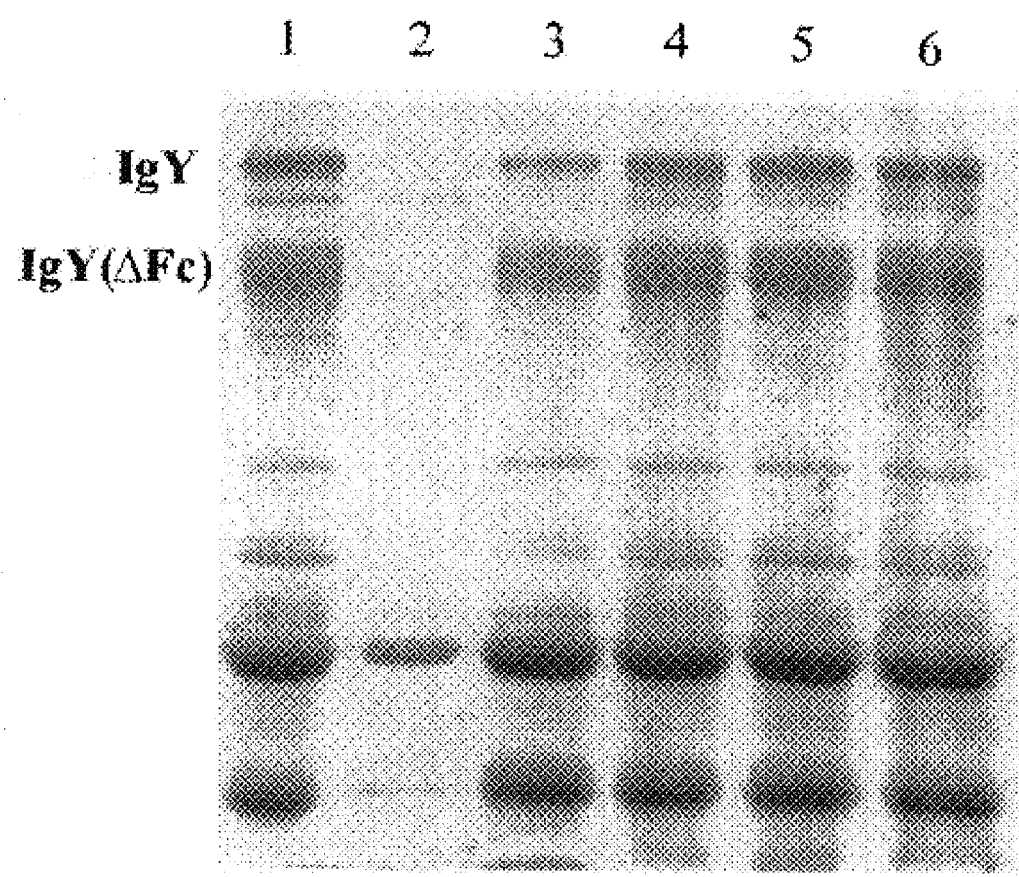
FIG. 1 illustrates a SDS-PAGE analysis comparing the antibody capturing abilities of four absorbents: lane 1, the partially purified antibody extract; lane 2, the solution flowing through 2% flamed silica; lane 3, the solution flowing through 3% silica dioxide; lane 4, the solution flowing through 3% Ceite diatomite; lane 5, the solution flowing through 3% Ceite diatomite hyflo-Cel; and lane 6, the solution flowing through 5% Celite diatomite hyflo-Cel.

The yolk antibodies are abundant in the bird serum and the eggs laid by the bird. However, as described above, collection of the antibody from the egg is usually preferred on account of the cost. The laying hen transfers both of the IgY and IgY(ΔFc) isoforms from serum to the egg yolk. In principle, each duck egg contains about 1–4 mg IgY/ml and about 3–12 mg IgY(ΔFc)/ml in the yolk and, therefore, the total quantity of the antibodies contained in a single egg is estimated to be 15–80 mg of IgY and 45–240 mg of IgY(ΔFC). The large volume of egg yolk produced vastly exceeds the volume of the serum that can be safely obtained from the birds over any given time period. In addition, extraction of yolk antibodies can be performed on a large scale without costly investment.

In accordance with the present invention, there is provided a process for efficiently isolating antibodies from egg yolk, in which the so-called "adsorption chromatography" or "differential salting-out," which may be used alone or in combination with the other, acts as a critical step during the isolation.

As used herein, the term "adsorption chromatography" is directed to a type of separation method involving the use of a stationary phase to selectively take up and concentrate the desired solutes from a mobile phase. According to one aspect of the present invention, a water insoluble non-charged absorbent acts as the active constituent in the stationary phase to trap water-miscible lipidic impurities normally present in egg yolk.

The adsorption chromatographic procedure according to the present invention is preferably preceded by a procedure of partial purification to remove the majority of the non-aqueous bio-molecules and large granules and preferably the majority of irrelevant proteins in the egg yolk. Any conventional method effective to achieve such a purpose is useful in the present invention, exemplary of which includes the use of an aqueous buffer or water to obtain an aqueous phase rich with antibodies, and the use of PEG, dextran sulfate or a natural gum, such as sodium alginate, carrageenan and xanthan gum, to coprecipitate the undesired substances.

In a preferred embodiment of the present invention, the yolk is firstly separated from the egg white, and then washed with distilled water to remove as much albumen as possible. The vitelline membrane encapsulating the yolk is punctured, and the separated yolk fraction is then diluted with an effective amount of an aqueous buffer or water to form a suspension of the egg yolk. Preferably, the collected egg yolk is diluted with an aqueous buffer solution or distilled water ranging from 2 parts to about 40 parts by volume, more preferably from 5 parts to about 30 parts by volume, per 1 part of the egg yolk. pH value is reported to be a critical factor during the stage of partial purification (E. M. Akita and S. Nakai, *J. Food Sci.* 57:629 (1993)). For the best recovery of yolk antibodies, pH is preferably set within a range of about 5–7. Desirably, the temperature in this step is within a range of about 0° C.–60° C. The suspension of the egg yolk is gently agitated to form a homogenous mixture, and then allowed to stand for a period of time sufficient to form the aqueous and non-aqueous phases. The water insoluble materials, including non-aqueous bio-molecules such as lipoproteins, phospholipids, sterols and the like, are then removed from the aqueous yolk suspension by centrifugation. The resulting antibody-containing supernatant may then be separated from the viscous precipitant by decanting, suctioning, or other like methods known in the art.

In general, the lipid content of the water-miscible fraction thus obtained is still so high as to be adverse to the subsequent manipulation. According to the present invention, a stationary phase containing a water insoluble non-charged absorbent is incubated with the water-miscible fraction in a sufficient amount to adsorb the majority of the water-miscible lipidic substances remaining in the water-miscible fraction. The suitable absorbents include but are not limited to fumed silica, amorphous silica, silica dioxide, silica gel, silicates, diatomaceous earth, Fuller's earth, talc, aluminas, activated carbon, aluminum oxide, titanium oxide, and other synthetic or natural clays that have the ability to physically adsorb lipids. Particularly preferred absorbents are fumed silica, silica dioxide and diatomaceous earth. The working ratio of the absorbent to the water-miscible fraction can vary over a wide range depending upon the properties of the absorbent chosen. When fumed silica is used in this process, it is preferably added to a concentration of equal to or higher than 0.1% by weight, and more preferably ranged between 0.3–5.0% by weight, based on the volume of the water-miscible fraction to be treated. When the absorbent is silica dioxide or diatomaceous earth, the adsorption chromatography according to this invention is preferably carried out at more than 1% by weight, and more preferably in a range of 3–20% by weight, of the absorbent based on the volume of the water-miscible fraction to be treated.

The adsorption chromatography according to this invention can be effectuated by any conventional ways, such as batch treatment of the water-miscible fraction with a absorbent or flowing the water-miscible fraction over a chromatography column packed with the absorbent, as long as the amount of the lipidic substances retained on the surfaces of the absorbent is satisfactory. The reaction time and temperature during the treatment are not critical to the results, and a reaction temperature of 4–30° C. and a reaction time of 10–60 minutes are usually feasible. While the adsorption procedure can be repeated several times, each with fresh absorbent, if necessary, a single operation is normally sufficient. By way of this procedure, the lipids and most of the non-lipid substances can be successfully separated into two immiscible phases.

Depending upon the capability of the selected absorbent to capture immunoglobulins, the yolk antibodies can be recovered from either an eluate eluted from the stationary phase or the "flow-through solution" which, as used herein, is intended to represent the solution passing through the stationary phase. As shown in the preferred embodiments given in the text, the yolk antibodies are mainly present in the stationary phase when fumed silica or silica dioxide is used as the absorbent, whereas diatomaceous earth leaves more than 90% of the antibodies in the flow-through solution.

The choice of a particular method to elute yolk antibodies can be determined by the skilled artisan. Typically, an eluent buffered at a pH of lower than 4 or higher than 8 or containing a chaotropic agent can be utilized in the present invention to elute out the yolk antibodies from the stationary phase without substantially dissociating the lipidic substances from the stationary phase, such that an antibody-containing eluate is formed. As used herein, the term "eluate" is directed to a solution containing the desired substances unbound by the eluent from the stationary phase. The term "chaotropic agent" or "chaotrope" is directed to a chemical capable of inducing a conformational change in a protein molecule, such as an antibody molecule, which is therefore often known as a protein denaturant. According to the invention, most of the bound antibodies can be successfully eluted with any neutral buffer containing moderate concentration (>1 M) of a chaotropic agent. In most instances, removal of the chaotrope after elution will restore the native protein structure.

The useful eluents include but are not limited to 0.1 M glycine-HCl, pH 2.3; 0.1 M glycine-HCl, pH 10.0; 6 M guanidine-HCl, pH 3.0; 3.0 M potassium chloride; 5 M potassium iodide; 3.5 M magnesium chloride; 1–3 M ammonium/sodium/potassium thiocyanate and 6 M urea. With respect to the activity of the recovered antibodies, however, a moderate-ionic strength, chaotrope-containing, neutral pH buffer, such as 3 M sodium thiocyanate buffered in 20 mM MES buffer (pH 5.8) or 20 mM Tris (hydroxymethyl)-aminomethane (pH 7.5), is more suitable for practicing the invention. The active state of the collected antibodies can be easily restored by, for example, extensive dialysis against a low-ionic strength, non-chaotrope-containing, weakly acidic buffer.

According to one aspect of the present invention, the eluate or the flow-through solution, which is enriched with antibodies, can subsequently be subjected to a procedure of differential salting-out to separate yolk antibody isoforms.

The term "salting-out" as used herein takes on its common meaning in the art of protein chemistry and is directed to the addition of a non-denaturing salt or salts to a mixture or production batch to decrease the solubility of proteins, which leads to the precipitation or coagulation of the proteins. By the term "differential salting-out" is meant a salting-out process that differentially precipitates or coagulates two or more proteins from a mixture by varying the concentration of the added salt or salts. In the present invention, the proteins intended to be differentially precipitated are the isoforms of yolk antibodies, i.e., IgY and IgY($\Delta$Fc). Examples of the non-denaturing salts useful for precipitation of the yolk antibodies include but are not limited to NaCl, $Na_2SO_4$, $(NH_4)_2SO_4$, KCl, $CaCl_2$, and $MgSO_4$. Preferably, the non-denaturing salt is $Na_2SO_4$ or $(NH_4)_2SO_4$, and $(NH_4)_2SO_4$ is the most preferred. The salt concentration for differentially precipitating yolk antibody isoforms depends on the type of the salt and can be determined by a skilled artisan through simple tests. According to a preferred embodiment of the present invention, in which $(NH_4)_2SO_4$ is employed, IgY is firstly salted out at a concentration of equal to or lower than 21% (w/v) of the salt on the basis of the treated volume of the eluate or the flow-through solution, while IgY($\Delta$Fc) is precipitated as the concentration of the salt is raised up to about 31% (w/v) based on the treated volume of the eluate or flow-through solution. It should be appreciated that the sequence of precipitation of the two antibody isoforms could be also variable depending on the salt chosen. The combined use of two or more salts in this procedure, e.g., firstly precipitating a first isoform with one salt followed by precipitating a second isoform with another salt, is also feasible. The differential salting-out procedure according to the present invention dramatically accomplishes a main object of the present invention, i.e., essential separation of the desired IgY($\Delta$Fc) antibodies from the whole population of yolk antibodies constituted by both IgY and IgY($\Delta$Fc).

If obtaining the antibodies with a higher purity is desired, the precipitated antibodies can be redissolved in a suitable buffer system and subjected to additional purification procedures, such as size exclusive chromatography, hydrophobic interaction chromatography, ion-exchange chromatography and immuno-affinity chromatography.

As used herein, the term "immunoaffinity purification" or "immunoaffinity chromatography" is directed to a type of separation method based on the binding characteristics of antibodies for a specific antigen. That is, the antibodies that bind to a specific antigen under a particular condition are separated from the unbound antibodies under that condition. The present invention contemplates the use of immunoaffinity purification to eliminate irrelevant proteins, in particular the non-antigen-binding immunoglobulin.

According to the present invention, the immunoaffinity purification is conducted by use of an "antigen matrix" comprised of antigen immobilized onto an insoluble support. The type of the support is not critical to the immunoaffinity purification of the invention. Any conventional support material suitable for the covalent attachment of an antigen and inert to the interaction between the desired antibody and the antigen immobilized thereon is useful. Usually, the support is made of crosslinked agarose or crosslinked dextran, such as the CNBr-activated Sepharose 4B commercially available from Pharmacia.

The antibodies purified by differetial salting-out is dissolved in a "binding buffer" and applied onto the antigen matrix, so that the immuno-complexes of the immobilized antigen and the yolk antibodies are formed. Any buffer system inert to the antigen-antibody interaction and effective to maintain the desired binding condition is useful in the present invention. Preferably, the binding buffer is selected from the group consisting of a phosphate buffer, an MES (2-[N-morpholino]ethanesulfonic acid) buffer and a bis-Tris buffer, among which an MES buffer at a concentration of 20 mM is the most preferred.

Preferably, the immunoaffinity purification is conducted in an environment of weak acid and low ionic strength, i.e., at pH within a range of 4–7 and under an ionic strength of lower than 50 mM. More preferably, the antibodies were allowed to interact with the immobilized antigen at pH within a range of 5–6 and most preferably within a range of 5.6–5.8. The yolk antibodies can be dissociated from the antigen matrix by a chaotropic salt, or at a pH of lower than 4 or higher than 8. The activity of the collected antibodies can be restored by, for example, extensive dialysis against a low-ionic strength, non-chaotrope-containing, weakly acidic buffer.

The IgY($\Delta$Fc) purified according the method of the invention neither activate the complement system nor binds to rheumatoid factor of mammalian sera. The immunological cross-reactivity between IgY($\Delta$Fc) and the mammalian IgG is not significant. Thus, the invention also provide a new type of antibody suitable for clinical and research uses.

The invention also provides a broad variety of clinical and research uses of the IgY(ΔFc) antibody prepared according to the invention.

For example, the present invention provides a method for immunizing an animal (which includes domestic fowls, livestock and companion animals) or human patient by administering to the patient a therapeutic amount of the the IgY(ΔFc) antibody of the present invention to protect them from various etiological agents, including microorganisms, such as bacteria, native, recombinant or peptide-synthetic viruses, fungi, protozoa, nematodes and the like, and proteinaceous or non-proteinaceous substances, such as native, recombinant or peptide-synthetic allergens, toxins, venoms, hormones or any other immunogen capable of eliciting an immune response. Preferably, the purified IgY(ΔFc) antibody is administered in combination with a pharmaceutically acceptable carrier such as water, saline and the like.

The IgY(ΔFc) antibody of the present invention is also useful for detecting an etiological agent of interest, including, for example, a pathogenic or non-pathogenic organism, such as *Escherichia coli, Salmonella enteritis,* and other bacterial organisms; a native, recombinant or peptide-synthetic hormone such as estrogen, progesterone, thyroxin and the like; a major histocompatibility complex antigen and the like; a native, recombinant or peptide-synthetic tumor marker such as alpha-fetoprotein, prostate specific antigen and the like; a disease state marker such as C-reactive protein, ferritin and the like; in a body sample such as a fluid, tissue, cell extract and the like, that is derived from the human or animal. Using the IgY(ΔFc) antibody obtained according to this invention, an etiological agent of interest can be quantitatively or qualitatively detected by any conventional method known in the art, such as the Ouchterlony methods (MO), the single radial immuno diffusion method (SRID), the immuno electrophoresis method (IEP), the radioimmuno assay method (RIA), the enzyme-linked immuno sorbent assay method (ELISA), the Western blot method (WB), the turbidimetric immunoassay method (TIA), the particle-enhanced turbidimetric immunoassay method, an enzymatic immunoassay, a nephelometric immunoassay, a chemiluminescent immunoassay, an immuno gold assay, or an immuno-chromatography assay.

The IgY(ΔFc) antibody of the present invention is also adapted for use in biochips and biosensors.

PREFERRED EMBODIMENTS FOR PRACTICING THE INVENTION

The following Examples are given for the purpose of illustration only and are not intended to limit the scope of the present invention.

EXAMPLE 1

Immunization Procedure for Stimulation of Specific Antibody Production

Twelve, 16-week old, domestic ducks (*Anas platyrhynchos* var. *domestics*) were individually housed for antibody and egg production. The ducks received an initial subcutaneous injection of 1–5 mg/ml of human C-reactive protein (CRP; purified from human ascites) in phosphate buffer, pH 7.5 emulsified with an equal volume of complete Freund's adjuvant. The concentration of the antigen used was generally in the range of 1 to 5 mg/ml. After the initial injection, young hens received three additional injections of 1–5 mg of antigen every two weeks. One week later, eggs began to be collected, labeled and stored at 4° C. until processed for extraction and purification of antibody. The booster procedure was repeated every four weeks during the experiment. Blood was sampled at the seventh day after each booster injection. Each blood sample was centrifuged and the resulting serum was collected.

EXAMPLE 2

Extraction of Antibodies from Duck Yolks

The yolks collected from the eggs laid by the hyperimmunized ducks of example 1 were thoroughly washed by a weak jet of distilled water, to thereby remove albumen. The volume of yolk was measured and then mixed thoroughly with distilled water in an amount of ten times the measured amount of yolk. The mixture was then held for at least two hours under 4° C., and subsequently centrifuged at 10,000 rpm in a Hitachi CR22F centrifuge for one hour. A pale supernatant layer and a semi-solid pliable layer were formed in centrifuge tubes.

EXAMPLE 3

Treatment with Absorbents

To the crude extract prepared in example 1 were added with one of the absorbents: 2% (w/v) fumed silica (purchased from Sigma), 3% (w/v) silica dioxide (sigma), 3% (w/v) Celite diatomite (purchased from Celite Corporation), and 3 or 5% (w/v) Celite diatomite hyflo-Cel (Celite Corporation). The resultant suspensions were incubated at 4° C. for 60 minutes with gentle stirring. After completion of the incubation, the absorbents were precipitated at 4° C. at 20,000 rpm in a Hitachi CR-22F centrifuge, and the supernatants and pellets were harvested separately. 10 μl samples taken from each supernatants were subjected to non-reducing sodium dodecyl sulfate polyacrylamide gel electrophoresis (SDS-PAGE).

As shown in FIG. 1, in terms of the quantity of the antibodies adsorbed by the absorbents, fumed silica has the best adsorptive activity and almost no antibody was left in the flow through solution. Silica dioxide displays a slightly weaker affinity to immunoglobulins, which perhaps results from its lower porosity (and thus comprising a less extensive surface area) than fumed silica. On the other hand, less than 10% of the yolk antibodies were captured by either type of the diatomaceous earths.

EXAMPLE 4

Differential Salting-out of Yolk Antibodies

Figure 2:
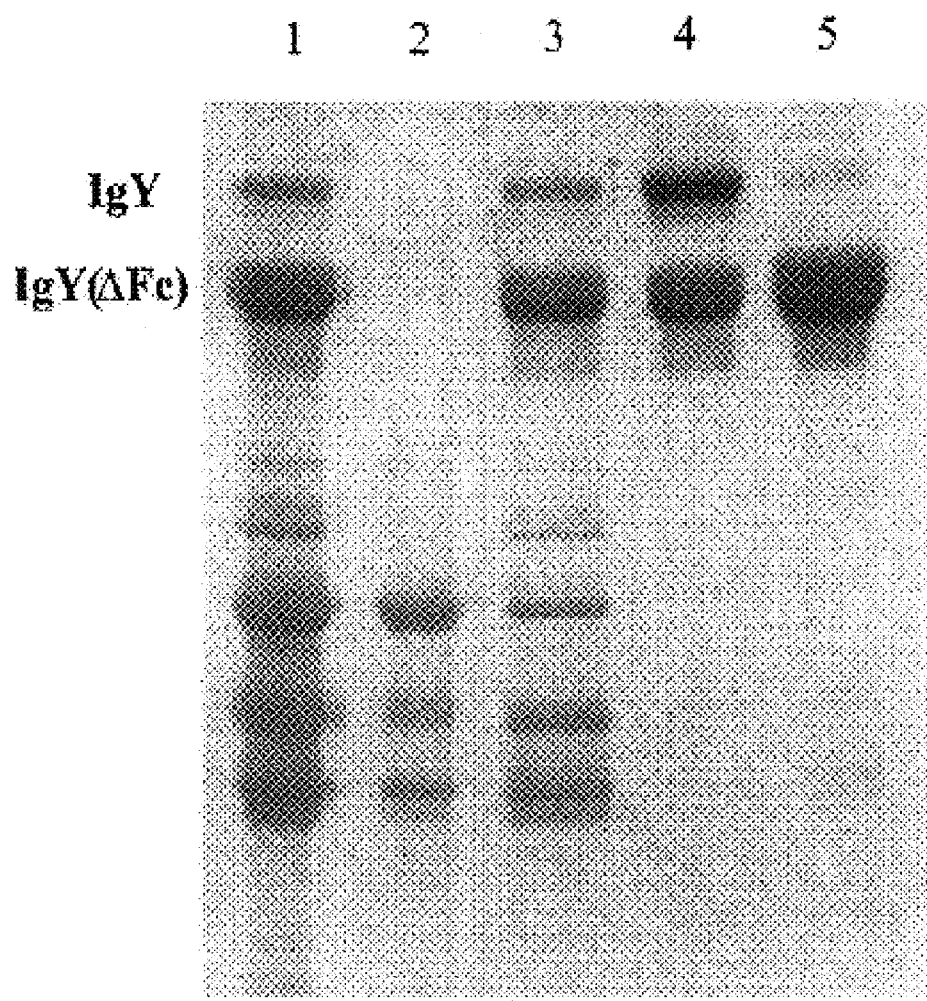
FIG. 2 illustrates the electrophoresis results of the purified yolk antibodies using fumed silica as the absorbent run on an 8% SDS-polyacrylamide gel: lane 1, the partially purified antibody extract; lane 2, the solution flowing through 2% fumed silica; lane 3, the eluate from the fumed silica pellet; lane 4, the antibody product precipitated with 21% (w/v) ammonium sulfate in the first precipitation step; and lane 5, the antibody product precipitated with 31% (w/v) ammonium sulfate in the second precipitation step.

The fumed silica pellet obtained in example 3 was treated with 2.5 M sodium thiocyanate (pH 7.5) to elute the antibodies bound thereon. The resultant eluate was firstly precipitated with ammonium sulfate at a concentration of about 21% (w/v) based on the volume of the eluate, followed by a second precipitation with addition of ammonium sulfate to about 31% (w/v). The precipitated antibody products were redissolved in phosphate buffer soline (PBS). Analytical SDS-PAGE was performed on a 8% non-reducing acrylamide gel, in which 2237 μg of the crude extract of example 2 (lane 1), 10 μl of the flow through harvested in example 3 (lane 2), 1122.25 μg of the eluate from the fumed silica pellet (lane 3), and 153 μg and 372.85 μg of the antibody products obtained in the first and second precipitation steps (lane 4 and lane 5, respectively) were loaded. The result is shown in FIG. 2. The percentage recovery and purity were determined by scanning densitometry of the gel and summarized in Table 1.

TABLE 1

|  | Total protein | IgY percentage | IgY yield/egg | IgY(ΔFc) percentage | IgY(ΔFc) yield/egg |
|---|---|---|---|---|---|
| crude extract | 447.4 mg | 4.43% | 19.82 mg | 26.79% | 119.86 mg |
| eluate | 224.45 mg | 8.15% | 18.29 mg | 41.65% | 93.48 mg |
| 1st precipitation by 21% (NH$_4$)SO$_4$ | 30.65 mg | 37.82% | 11.59 mg | 62.18% | 19.06 mg |
| 2nd precipitation by 31% (NH$_4$)SO$_4$ | 74.57 mg | 2.03% | 1.51 mg | 96.62% | 72.05 mg |

As illustrated in Table 1, the resulting IgY(ΔFc) antibodies are recovered in about 76% yield (72.05 mg/119.86 mg×100%) in greater than 96% purity. More importantly, this purification scheme advantageously leads to the essential separation of the desired IgY(ΔFc) antibodies from the whole population of yolk antibodies constituted mainly by both IgY and IgY(ΔFc).

EXAMPLE 5

Immunoaffinity Purification of Yolk Antibodies

Figure 3:
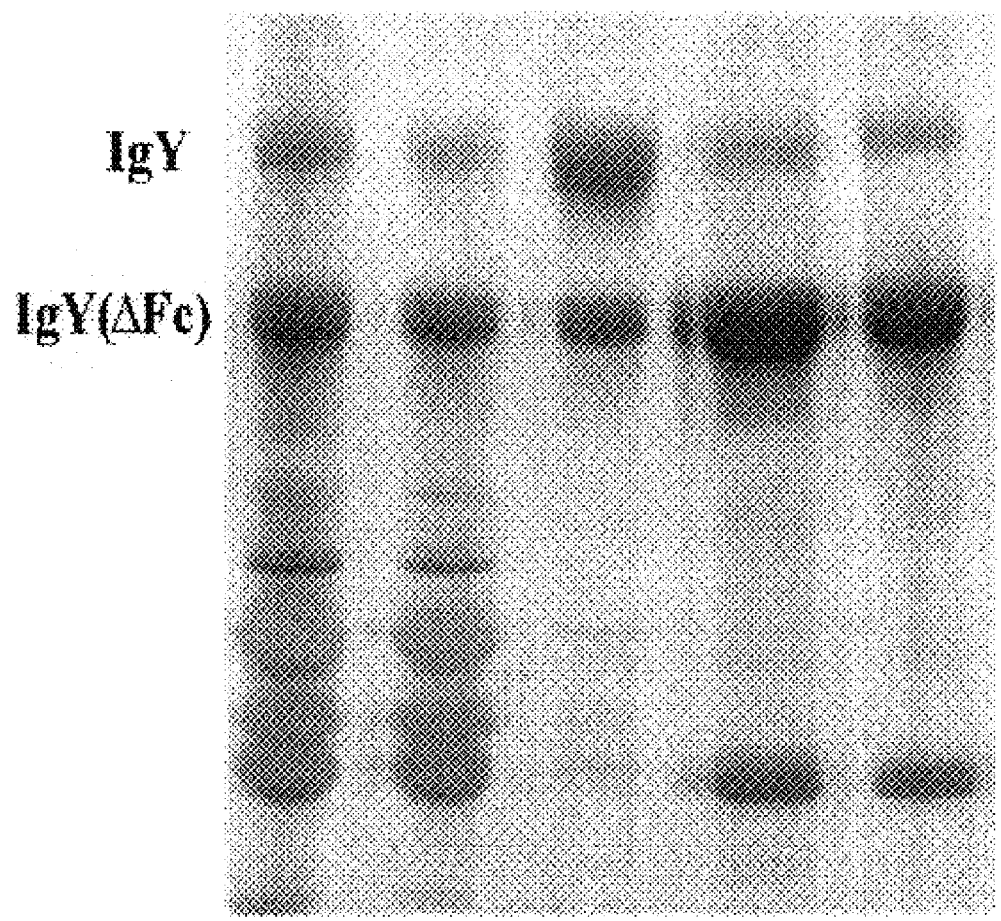
FIG. 3 illustrates the electrophoresis results of the purified yolk antibodies using Celite diatomite as the absorbent run on an 8% SDS-polyacrylamide gel: lane 1, the partially purified antibody extract; lane 2, Celite diatomite filtrate; lane 3, the antibody product precipitated with 21% (w/v) ammonium sulfate in the first precipitation step; lane 4, the antibody product precipitated with 31% (w/v) ammonium sulfate in the second precipitation step; and lane 5, the antibody product precipitated with 16% (w/v) sodium sulfate in the second precipitation step.

Taking advantage of the ability of diatomaceous earth to attract lipids and repulse antibodies, the crude extract prepared in example 2 was poured onto a filtration column packed with 10% by weight of Celite diatomite based on the poured volume of the extract. The solution flowing through the column was harvested and subjected a first precipitation with 21% (w/v) ammonium sulfate based on the volume of the flow through solution. The precipitated antibodies were collected and the supernatant was divided into two parts. One part of the supernatant was precipitated with ammonium sulfate at a concentration of about 31% (w/v), while the other part was precipitated with 16% (w/v) sodium sulfate. The precipitated antibody products were redissolved in PBS. Analytical SDS-PAGE was performed on a 8% non-reducing acrylamide gel, in which 2012.5 μg of the crude extract of example 2 (lane 1), 1678 μg of the flow through harvested by Celite diatomite filtration (lane 2), 94.9 μg of the eluate obtained in the first precipitation step (lane 3), and 169.65 μg and 357.75 μg of the antibody products obtained in the second precipitation step by 31% ammonium sulfate and 16% sodium sulfate (lanes 4–5) were loaded. The result is shown in FIG. 3. The percentage recovery and purity were determined by scanning densitometry of the gel and summarized in Table 2.

As illustrated in Table 2, the resulting IgY(ΔFc) antibodies are recovered in about 77% (when sodium sulfate is used in the second precipitation step) and 69% purity (when ammonium sulfate is used in the second precipitation step), respectively, with high yields.

EXAMPLE 6

Immunoaffinity Purification of Yolk Antibodies

A C-reactive protein (CRP) solution was prepared in 0.1 M carbonate buffer, pH 8.5 at a concentration of 5 mg/ml. CNBr-activated Sepharose 4 B purchased from Pharmacia was washed initially with 1 mM cold HCl in an amount of ten times the matrix volume and allowed to react with the CRP solution in an amount of two times the matrix volume of at 4° C. overnight. The antigen matrix was suspended in a solution of 0.5 M ethanolamine in 20 mM Tris-HCl (pH 8.5) in a ratio of 1:1 (v/v) for 2 hours at 4° C. to block remaining protein-reactive sites. The antigen matrix was then washed with PBS containing 0.02% sodium azide and stored at 4° C.

Figure 4:
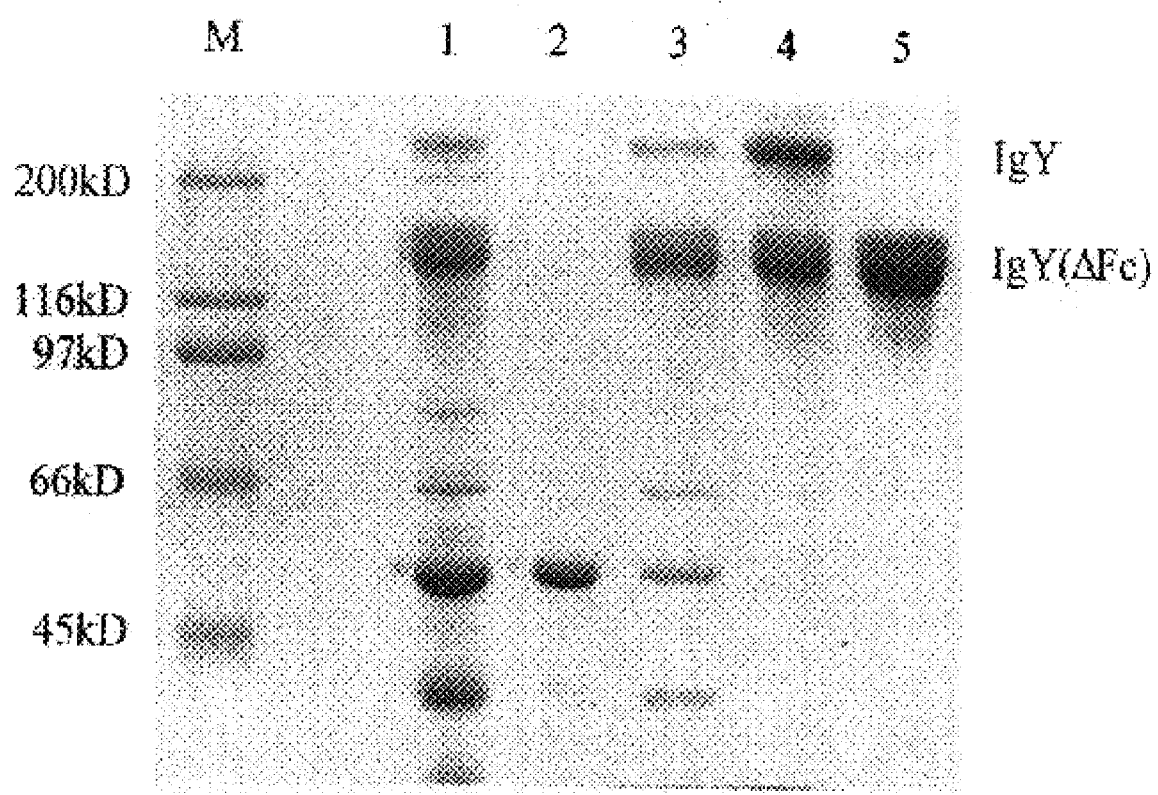
FIG. 4 illustrates the electrophoresis results of the purified yolk antibodies using fumed silica as the absorbent run on an 8% SDS-polyacrylamide gel: M, molecular weight marker; lane 1 the partially purified antibody extract; lane 2, the solution flowing through 2% fumed silioa lane 3, the eluate from the finned silica pellet; lane 4, the antibody product precipitated with 21% (w/v) anunonium sulfate; and lane 5, the antibody product purified by affinity chromatography.

The duck antibodies precipitated with 21% (w/v) ammonium sulfate in example 4 and the antigen matrix prepared above were used. One ml of the antigen matrix was packed into a conventional column and soaked in 20 mM of MES (2-[N-morpholino]ethanesulfonic acid) buffer (pH 5.8). The antigen matrix was allowed to react with 0.25 ml of the antibodies formulated in the same binding buffer. The antigen matrix was washed with the binding buffer until the effluent was substantially free of protein. Bound antibodies were eluted immediately with 6 M guanidine-HCl, and the optical density thereof was measured at 280 nm after a complete dialysis. The SDS-PAGE analysis shown in FIG. 4 indicates that the affinity-purified antibodies are constituted mainly by IgY(ΔFc) antibody which is represented by a single band on the gel.

TABLE 2

|  | Total protein | IgY percentage | IgY yield/egg | IgY(ΔFc) percentage | IgY(ΔFc) yield/egg |
|---|---|---|---|---|---|
| crude extract | 405.2 mg | 11.60% | 46.98 mg | 29.01% | 117 mg |
| CLT filtrate | 335.6 mg | 5.08% | 17.05 mg | 30.47% | 102.25 mg |
| 1st precipitation by 21% (NH$_4$)SO$_4$ | 18.98 mg | 62.60% | 11.88 mg | 37.40% | 7.10 mg |
| 2nd precipitation by 16% Na$_2$SO$_4$ | 33.93 mg | 6.29% | 2.13 mg | 77.14% | 26.17 mg |
| 2nd precipitation by 31% (NH$_4$)SO$_4$ | 71.55 mg | 8.79% | 6.29 mg | 68.68% | 49.14 mg |

All patents and literature references cited in the present specification are hereby incorporated by reference in their entirety. In case of conflict, the present description, including definitions, will prevail.

While the invention has been described with reference to the above specific embodiments, it should be recognized that various modifications and changes, which will be apparent to those skilled in the relevant art, may be made without departing from the spirit and scope of the invention.

We claim:

1. A process for selectively isolating antibody isoforms from egg yolk, the process comprising:
   (i) obtaining an aqueous fraction of egg yolk from a fowl hen egg;
   (ii) treating the aqueous fraction with a $(NH_4)_2SO_4$ salt at a first concentration to provide a precipitate comprising a major portion of a first antibody isoform from the aqueous fraction and a resultant supernatant comprising a second antibody isoform; and
   (iii) salting out a major portion of the second antibody isoform from the resultant supernatant by adjusting the resultant supernatant with $(NH_4)_2SO_4$ salt at a second concentration,
   wherein the first concentration is no more than about 21% (w/v) $(NH_4)_2SO_4$ based on the volume of the aqueous fraction treated in step (ii), and the second concentration is about 31% (w/v) $(NH_4)_2SO_4$ based on the volume of the resultant supernatant in step (iii), and the first antibody isoform is IgY, the second antibody isoform is IgY($\Delta$Fc), and the ratio of IgY($\Delta$Fc) antibodies to IgY antibodies in the salted-out material comprising the major portion of the second antibody isoform is greater or equal to 7.81.

2. The process of claim 1, wherein the aqueous fraction of step (i) is obtained from a pretreatment including the steps of:
   (a) removing non-aqueous bio-molecules and granules from the egg yolk of a fowl hen egg to thereby obtain a water-miscible fraction containing yolk antibodiers;
   (b) passing the water-miscible fraction through a stationary phase containing an effective amount of a water insoluble non-charged absorbent capable of adsorbing water-miscible lipidic substances normally present in egg yolk; and
   (c) collecting for use as the aqueous fraction the solution which has flowed through the stationary phase.

3. The process of claim 2, wherein the removing step (a) includes diluting the egg yolk with an effective amount of a diluting agent selected from a group consisting of an aqueous buffer solution and water, and subsequently subjecting the resultant diluted egg yolk to separation treatment, to thereby remove the non-aqueous bio-molecules and granules.

4. The process of claim 3, wherein said effective amount of the diluting agent is ranging from 5 parts to 30 parts by volume per 1 part of the egg yolk.

5. The process of claim 2, wherein the absorbent is selected from the group consisting of fumed silica, silica dioxide and diatomite earth.

6. The process of claim 2, further comprising a step of eluting the stationary phase to obtain an eluate for use as the aqueous fraction.

7. The process of claim 6, wherein the eluate is eluted from the stationary phase by a chaotropic salt.

8. The process of claim 7, wherein the chaotropic salt is selected from the group consisting of 6 M guanidine-HCI and 1–3 M sodium thiocyanate.

9. The process of claim 6, wherein the eluate is elated from the stationary phase at a pH of lower than 4 or higher than 8.

10. The process of claim 1, which is followed by one or more purification procedure selected from the group consisting of size exclusive chromatography, hydrophobic interaction chromatography, ion-exchange chromatography and immuno-affinity chromatography.

11. The process of claim 10, wherein the purification procedure is immuno-affinity chromatography.

12. The process of claim 11, wherein the immuno-affinity chromatography is conducted at pH 4–7 and under an ionic strength of lower than 50 mM.

13. The process of claim 12, wherein the immuno-affinity chromatography is conducted at pH 5.6–5.8.

14. The process of claim 1, wherein the egg yolk is derived from the egg of a fowl hen immunized with a selected antigen.

15. The process of claim 14, wherein the fowl hen is an anseriform bird.

16. The process of claim 15, wherein the fowl hen is a duck.

17. A process for selectively isolating antibodies from egg yolk, the process comprising:
   (a) removing non-aqueous bio-molecules and granules from egg yolk of a fowl hen egg to thereby provide a water-miscible fraction comprising yolk antibodies;
   (b) passing the water-miscible fraction through a stationary phase containing an effective amount of water insoluble, non-charged absorbent capable of absorbing water-miscible lipid substances;
   (c) collecting a flow-through solution comprising yolk antibodies from the stationary phase;
   (d) treating the flow-through solution with a $(NH_4)_2SO_4$ salt at a first concentration to provide a precipitate comprising a major portion of a first antibody isoform from the aqueous fraction and a resultant supernatant comprising a second antibody isoform; and
   (e) salting out a major portion of the second antibody isoform from the resultant supernatant by adjusting the resultant supernatant with $(NH_4)_2SO_4$ salt at a second concentration, wherein the first concentration is no more than about 21% (w/v) $(NH_4)_2SO_4$ based on the volume of the aqueous fraction collected in step (c), and the second concentration is about 31% (w/v) $(NH_4)_2SO_4$ based on the volume of the resultant supernatant from step (d), and the first antibody isoform is IgY, the second antibody isoform is IgY($\Delta$Fc), and the ratio of IgY($\Delta$Fc) antibodies to IgY antibodies in the salted-out material comprising the major portion of the second antibody isoform is greater or equal to 7.81.

18. The process of claim 1, which is followed by at least one purification procedure selected from the group consisting of size exclusive chromatography, hydrophobic interaction chromatography, ion-exchange chromatography and immuno-affinity chromatography.

19. The process of claim 18, wherein the at least one purification procedure is immuno-affinity chromatography.

20. The process of claim 19, wherein the immuno-affinity chromatography is conducted at pH 4–7 and under an ionic strength of lower than 50 mM.

21. The process of claim 20, wherein the immuno-affinity chromatography is conducted at pH 5.6–5.8.

22. The process of claim 17, wherein the fowl hen is an anseriform bird immunized with a selected antigen.

23. The process of claim 22, wherein the fowl hen is a duck.

24. A process for selectively isolating antibodies from egg yolk, the process comprising:

(a) removing non-aqueous bio-molecules and granules from egg yolk of a fowl hen egg to thereby provide a water-miscible fraction comprising yolk antibodies;

(b) passing the water-miscible fraction through a stationary phase containing an effective amount of a water insoluble, non-charged absorbent capable of absorbing water-miscible lipid substances and yolk antibodies;

(c) eluting the yolk antibodies from the stationary phase as an eluate;

(d) treating the eluate solution with a $(NH_4)_2SO_4$ salt at a first concentration to provide a precipitate comprising a major portion of a first antibody isoform from the aqueous fraction and a resultant supernatant comprising a second antibody isoform; and (e) salting out a major portion of the second antibody isoform from the resultant supernatant by adjusting the resultant supernatant with $(NH_4)_2SO_4$ salt at a second concentration, wherein the first concentration is no more than about 21% (w/v) $(NH_4)_2SO_4$ based on the volume of the aqueous fraction collected in step (c), and the second concentration is about 31% (wAr) $(NH_4)_2SO_4$ based on the volume of the resultant supernatant from step (d), and wherein the first antibody isoform is IgY, the second antibody isoform is IgY (ΔFc), and the ratio of IgY(ΔFc) antibodies to IgY antibodies in the salted-out material comprising the major portion of the second antibody isoform is greater or equal to 7.81.

25. The process of claim 24 further comprising a purification procedure selected from the group consisting of size exclusive chromatography, hydrophobic interaction chromatography, ion-exchange chromatography and immuno-affinity chromatography.

26. The process of claim 25, wherein the purification procedure comprises immuno-affinity chromatography.

27. The process of claim 26, wherein the immuno-affinity chromatography is conducted at pH 4–7 and under an ionic strength of lower than 50 mM.

28. The process of claim 27, wherein the immuno-affinity chromatography is conducted at pH 5.6–58.

29. The process of claim 24, wherein the fowl hen is an anseriform bird immunized with a selected antigen.

30. The process of claim 29, wherein the fowl hen is a duck.

31. The process of claim 17 wherein the water insoluble, non-charged absorbent is diatomite earth.

32. The process of claim 24 wherein the eluting comprising contacting the stationary phased with a chaotropic salt.

33. The process of claim 32 wherein the chaotropic salt is guanidine HCl.

34. The process of claim 32 wherein the chaotropic salt is sodium thiocyanate.

35. The process of claim 24 wherein the water insoluble, non-charged absorbent is fumed silica.

36. The process of claim 24 wherein the water insoluble, non-charged absorbent is silica dioxide.

* * * * *